United States Patent [19]

Decoste

[11] Patent Number: 5,129,901
[45] Date of Patent: Jul. 14, 1992

[54] CANNULATED ORTHOPEDIC SCREW

[76] Inventor: Vern X. Decoste, 794 East Collins, Oxnard, Calif. 93030

[21] Appl. No.: 712,414

[22] Filed: Jun. 10, 1991

[51] Int. Cl.⁵ ............................................. A61B 17/58
[52] U.S. Cl. .................................... 606/65; 606/62; 606/73
[58] Field of Search ..................... 606/59, 65, 66, 72, 606/73; 408/227, 715; 411/387, 386, 417, 418, 419, 423

[56] References Cited

U.S. PATENT DOCUMENTS

| | | | |
|---|---|---|---|
| 1,330,792 | 2/1920 | Frick | 411/387 |
| 2,121,193 | 6/1938 | Hanicke | 128/92 |
| 2,267,925 | 12/1941 | Johnston | 128/92 |
| 2,489,870 | 11/1949 | Dzus | 128/92 |
| 2,699,774 | 1/1955 | Livingston | 128/92 |
| 3,044,341 | 7/1962 | Stern | 411/386 |
| 3,094,895 | 6/1963 | Broberg | 411/417 X |
| 3,783,860 | 1/1974 | Burstein et al. | 128/92 |
| 4,013,071 | 3/1977 | Rosenberg | 128/92 |
| 4,414,966 | 11/1983 | Stednitz | 128/92 |
| 4,468,200 | 8/1984 | Münch | 433/174 |
| 4,537,185 | 8/1985 | Stednitz | 128/92 |
| 4,568,229 | 2/1986 | Hulsey | 411/387 |
| 4,640,271 | 2/1987 | Lower | 606/73 X |
| 4,649,918 | 3/1987 | Pegg et al. | 128/305 |
| 4,653,486 | 3/1987 | Coker | 128/92 |
| 4,772,286 | 9/1988 | Goble et al. | 623/13 |
| 4,940,467 | 7/1990 | Tronzo | 606/66 |
| 4,950,270 | 8/1990 | Bowman et al. | 606/72 |
| 4,978,350 | 12/1990 | Wagenknecht | 606/73 X |

FOREIGN PATENT DOCUMENTS

| | | | |
|---|---|---|---|
| 666398 | 7/1988 | Switzerland | 606/73 |
| 463446 | 6/1975 | U.S.S.R. | 606/65 |
| 1316157 | 5/1973 | United Kingdom | 411/387 |
| 2178986 | 2/1987 | United Kingdom | 411/387 |

Primary Examiner—Robert A. Hafer
Assistant Examiner—Kevin G. Rooney
Attorney, Agent, or Firm—Nixon & Vanderhye

[57] ABSTRACT

A self-tapping, self-drilling cannulated screw, for orthopedic bone surgery, has tip, shank, threaded and head portions. The tip portion includes circumferentially spaced cutting points defining end surfaces which taper approximately 17° relative to a perpendicular to the screw axis to butt the distal end of the cutting edge of a cutting flute. The cutting flutes are formed at circumferentially spaced positions about the screw adjacent the tip portion and, upon insertion of the screw, efficiently direct chips through the threaded portions and past the shank portion. Reverse cutting flutes are provided at the opposite end of the threaded portion for cutting and forming threads upon unthreading and hence removal of the screw from the bone when healed.

18 Claims, 1 Drawing Sheet

CANNULATED ORTHOPEDIC SCREW

BACKGROUND AND SUMMARY OF THE INVENTION

The present invention relates to a cannulated screw for orthopedic bone surgery and particularly relates to a self-drilling, self-tapping cannulated screw designed to minimize or eliminate the danger of thermal necrosis, afford efficient chip removal both during insertion and removal, and generally facilitate insertion of the screw into the bone and its removal.

Many and various types of supposed self-drilling screws have been designed and used in the past. Many of these self-drilling screws require pre-drilling before insertion of the screw or the screw must be run in and out multiple times at progressively increasing depths before the screw can be finally seated. The latter is a result of chip loading on the screw during insertion causing the self-tapping screws to load up with chips and preventing further insertion of the screw into the bone. Moreover, upon attempted further insertion, oftentimes the threads will strip. Resorting to multiple in-and-out movements of the screw relative to the bone also results in wearing the threads, which increases the tendency for inaccurately placed bore holes and the danger of heat build-up during use.

Many such screws are designed with problems of screw insertion in mind but neglect the problems of removing the screw from the healed bone. It will be appreciated that the bone, upon healing, grows about the screw and thus it is necessary to withdraw the screw similarly as when inserting the screw by cutting the bone.

In accordance with the present invention, there is provided a cannulated, self-tapping, self-drilling screw, preferably for orthopedic bone surgery, which includes a shaft having tip, head and self-tapping threaded and shank portions. The screw is cannulated, i.e., it has an axial bore through the entire length of the screw opening through the head and tip portions. The screw includes a pair of cutting points (more than two cutting points may be provided) which are designed to self-drill to provide a proper tap hole ahead of the advancing self-tapping thread design of the threaded portion. The points feature a free cutting action reducing heat build-up at the cutting site and afford efficient chip rejection and removal, eliminating chip loading problems which can interfere with the ease and timeliness of the pin insertion. A pair of side flutes are formed in the screw threaded portion, the ends of the flutes terminating in the cutting points. The outer surfaces of the screw between each of the points and the first of the self-tapping screw threads extend circumferentially about the screw to terminate at a circumferentially adjacent flute, such outer surfaces forming an angle of between about 5°–7° with the axis of the screw. It has been found that this angle is critical and preferably is about 6°. A larger angle than, for example, about 7°, slows the cutting action and creates greater heat. A lesser angle, for example, of less than 5°, fails to clear the chips, necessitating multiple runs in and out. Hence, this slightly conical outer surface, which is interrupted by the flutes, has been found to be most effective in reducing heat and carrying chips away from the cutting site. The distal end of the tip also has surfaces which face in the axial direction of the screw. These surfaces extend from the cutting point, preferably at an angle of about 17°, circumferentially about the screw to terminate at the circumferentially adjacent cutting edge at a location axially inwardly of the point of the adjacent cutting edge. This facilitates the cutting action with minimal heat build-up.

The threaded portion of the screw also carries at least a pair of reverse cutting flutes at circumferentially spaced positions thereabout and spaced axially back from the flutes adjacent the tip portion. The cutting edges of the reverse cutting flutes are arranged to cut through the bone upon unthreading the screw from the bone. The reverse cutting edges start at an axial location adjoining the smooth shank of the screw whereby the reverse cutting edges tap the bore hole in which the screw resides during unthreading of the screw. The curved surfaces on the cutting edges of the flutes assist in removing the chips and funneling the chips into the threads for efficient removal and prevention of lock-up due to chip compaction. The head of the screw is provided with external flats, i.e., preferably in a hexagonal configuration, such that a tool may be applied externally about the head for both threading and unthreading rotations.

In a preferred embodiment according to the present invention, there is provided a cannulated self-tapping, self-drilling screw for orthopedic bone surgery comprising an elongated shaft having an elongated axis and tip, head, self-tapping threaded, and shank portions, the screw-threaded portion being disposed adjacent the tip portion and the shank portion disposed between the head and the screw-threaded portions. The shaft defines a cannula extending coaxially through the shaft and opening through the tip and the head portions. A plurality of flutes are formed in the screw-threaded portion at circumferentially spaced positions thereabout and interrupt the threads thereof to define self-tapping cutting edges along the interrupted threads for threading the screw into the bone, the tip portion including a pair of circumferentially spaced cutting points at the distal end of the tip portion, the distal end of the tip portion having end surfaces facing generally axially of the screw with each end surface extending from a cutting point at a predetermined angle circumferentially about the screw to terminate at a circumferentially adjacent cutting edge at a location axially inwardly of the point of the adjacent cutting edge. The outer surface of the screw between each point and the first of the self-tapping screw threads of the tip portion extends circumferentially about the screw, terminating at a circumferentially adjacent flute and forming an angle of between about 5–7 degrees with the axis of the screw.

In a further preferred embodiment according to the present invention, there is provided a cannulated self-tapping, self-drilling screw for orthopedic bone surgery comprising an elongated shaft having an elongated axis and tip, head, self-tapping threaded, and shank portions, the screw-threaded portion being disposed adjacent the tip portion and the shank portion disposed between the head and the screw-threaded portions. The shaft defines a cannula extending coaxially through the shaft and opening through the tip and the head portions. A plurality of flutes are formed in the screw-threaded portion at circumferentially spaced positions thereabout and interrupt the threads thereof to define self-tapping cutting edges along the interrupted threads for threading the screw into the bone. The tip portion includes a pair of circumferentially spaced cutting points at the distal end thereof, the outer surface of the screw between each point and the first of the self-tapping screw threads of the tip portion extending circumferentially about the screw and forming an angle of between about 5-7 degrees with the axis of the screw. At least a pair of reverse cutting flutes are disposed in the threaded portion of the screw, the reverse cutting flutes being circumferentially spaced one from the other, spaced axially from the plurality of flutes and interrupting the threaded portion to define reverse cutting edges for cutting bone upon unthreading the screw from the bone.

Accordingly, it is a primary object of the present invention to provide a novel and improved self-tapping, self-drilling cannulated screw for orthopedic bone surgery which minimizes or eliminates the danger of heat build-up at the cutting site, affords efficient chip removal, eliminates chip loading problems which can interfere with the ease and timeliness of screw insertion and in general facilitates a quick one-step screw insertion and removal capability.

These and further objects and advantages of the present invention will become more apparent upon reference to the following specification, appended claims and drawings.

BRIEF DESCRIPTION OF THE DRAWING FIGURES

DETAILED DESCRIPTION OF THE DRAWING FIGURES

Reference will now be made in detail to a present preferred embodiment of the invention, an example of which is illustrated in the accompanying drawings.

Figure 1:
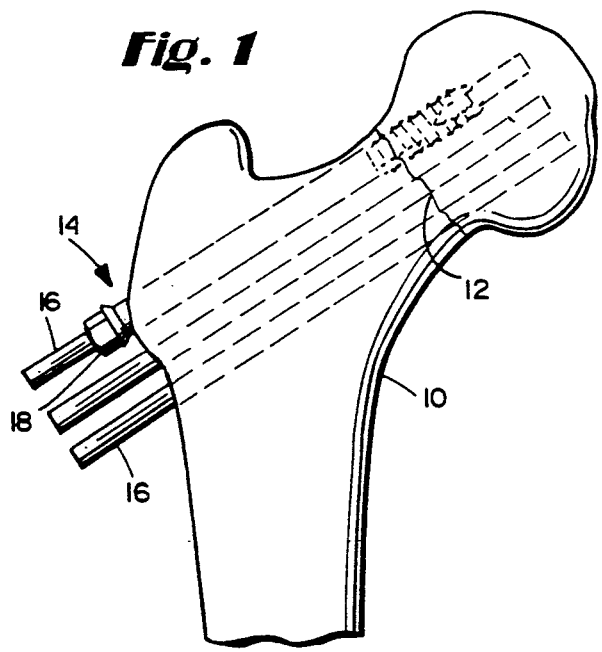
FIG. 1 is a fragmentary view of the femoral neck of a hip bone illustrating a fracture and guide pins inserted into the bone for facilitating application of a hip screw constructed in accordance with the present invention.

Referring now to the drawings, particularly to FIG. 1, there is illustrated a portion of a femoral hip bone 10 having a fracture 12. A hip screw, generally designated 14, is illustrated in position overlying a guide pin 16 previously inserted into the femoral head. Three guide pins 16 are illustrated and a jig, not shown, is normally used to ensure proper installation of the guide pins 16, the guide pins per se forming no part of the present invention. A cannulated guide screw 14 is placed over each guide pins and, by application of a suitable tool, also not shown, the screws are rotated for purposes of driving the self-tapping, self-drilling screws into proper position holding the portions of the bone together. When properly positioned, the guide pins 16 are removed. It will also be appreciated that after the healing process, the screws are removed.

Figure 2:
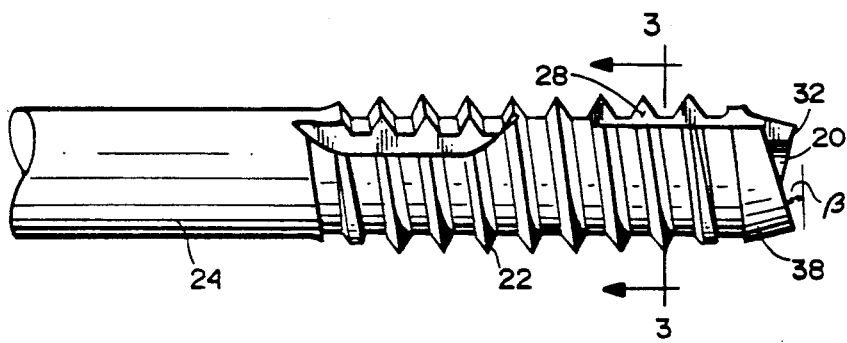
FIG. 2 is an enlarged fragmentary side elevational view of the tip, self-tapping threaded and shank portions of the orthopedic bone screw hereof.
Figure 4:
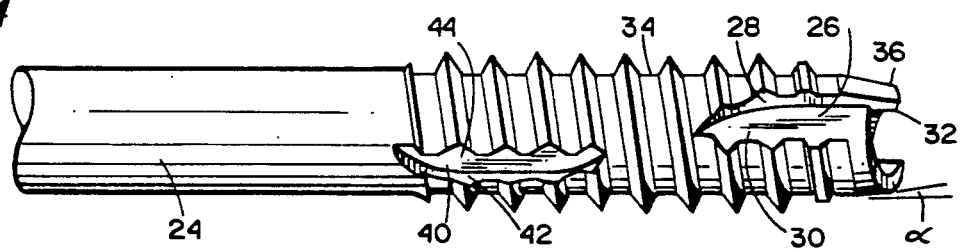
FIGS. 4 and 5 are views similar to FIG. 2 with the screw rotated to different axial positions to illustrate the cutting points, and cutting flutes.
Figure 5:
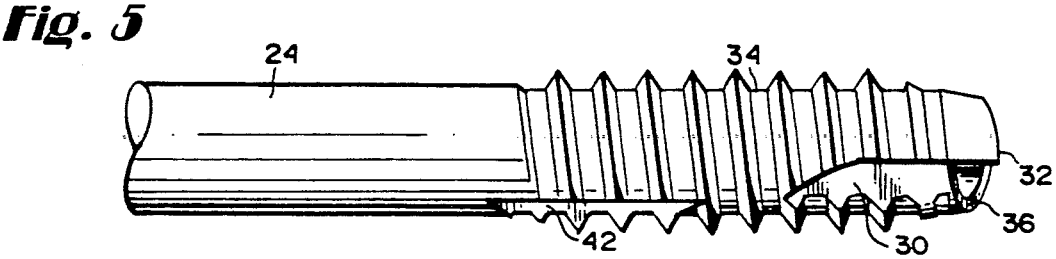

Referring to FIGS. 1 and 2, the cannulated screw hereof comprises head, tip, self-tapping threaded and shank portions 18, 20, 22 and 24, respectively. The threaded portion 22 is located between the tip portion 20 and shank portion 24, while the shank portion 24 is located axially between the threaded and head portions 22 and 18, respectively.

Figure 3:
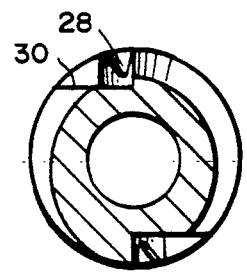
FIG. 3 is a cross-sectional view thereof taken generally about on lines 3—3 in FIG. 2.

A pair of cutting flutes 26 are formed in the threaded portion 22 adjacent the tip portion 20 and extend generally axially, terminating in the tip portion 20. It will be appreciated that more than two cutting flutes 26 may be provided and that the cutting flutes 26 are for purposes of cutting the bone to form screw threads, i.e., to tap the bone upon threading action of the cannulated screw into the bone. Each flute 26 interrupts a number of the threads of the threaded portion 22 and includes a generally radially extending wall 28 which serves as a cutting edge upon clockwise threading rotation of the screw into the bone. Wall 28 has an outer edge conforming to its intersection with the exterior surface of the threaded portion 22 whereby a tapped opening can be formed upon threading the screw 18 into the bone. The cutting edge 28 is also curved in the direction of rotation of the screw when threading the screw into the bone. The base 30 of each flute 26 extends along a chord line of the annular screw, as best illustrated in FIG. 3.

The cutting edge 28 terminates at its forward end in a cutting point 32. As illustrated, the cutting points 32 are spaced radially inwardly from the exterior surface of the roots 34 of the threaded portion 22. The points 32 form part of end surfaces 36 which face in an axial direction and extend from the cutting point 32 at a predetermined angle B, for example, about 17°, circumferentially about the screw to terminate a circumferentially adjacent cutting edge 28. An arcuate outer surface 38 defined between each point 32 and the first of the self-tapping screw threads 22 extends circumferentially about the screw to terminate at a circumferentially adjacent flute. That is, outer surfaces 38 extend axially between the end surfaces 36 and the first of the self-tapping screw threads 22 and between the circumferentially adjacent flutes. Each outer surface 38 forms an angle $\alpha$ between about 5° to 7° and preferably about 6° with the axis of the screw. The angle is indicated in an exaggerated form at $\alpha$. The outer surfaces thus form a circumferentially interrupted frusto-conical section.

At the opposite end of the threaded portion 22 from the tip of the screw, there is provided at least a pair of reverse cutting flutes 40. The reverse cutting flutes 40 are circumferentially spaced one from the other and, similarly as flutes 26, each comprises a radial cutting edge 42 and a flat 44 formed along a chord of the annular screw. Thus, radial cutting edge 42 is effective upon counterclockwise unthreading action of the screw to cut the healed bone, facilitating tapping of the screw whereby the screw may be readily removed from the bone. The cutting edge 42 is curved at its opposite ends to channel the chips into the threaded portions 22 upon removal of the screw.

Preferably, the screw is formed of a titanium alloy, although it will be appreciated that other, preferably lightweight metal materials may be used which are compatible with the human skeletal structure.

To employ the screw of the present invention, guide pins 16 are inserted into the femoral hip bone and through the fracture 12 in a conventional manner. Once inserted, a screw 14 is disposed concentrically about each guide pin. A driver, not shown, is engaged with the rear hex nut on the head 18 of screw 14 and the screw is driven under low speed, high torque, with careful pressure being applied. The tip portion 20 is designed to self-drill a properly sized tap hole ahead of the advancing self-tapping threaded portion 22. The taper of the outer surfaces 38 of the tip 20 is preferably between about 5° to 7° and most preferably 6°. If the taper is greater, the screw slows in its self-drilling capacity and creates additional unwanted heat. If the taper is a fewer number of degrees than 5°, the chips from the bone do not clear and multiple in-and-out action of the screw is required, with the chips being cleaned upon each withdrawal thereof. As the screw is advanced, the cutting edge 28 of the cutting flutes forms the female thread in the bone with the chips passing up and about the threaded portion 22 and into the annular space between the bone bore previously cut and shank portion 24. Note that the diameter of the shank portion 24 is less than the diameter of the threaded portion 22. Upon full seating of the screw in place about the pins 16, the pins 16 may be removed.

After healing, the screws 14 are removed by applying an opposite torque to the head portion 18. By rotating the screw in an unthreading direction, the cutting edges 42 of the flutes 44 cut the bone as the screw is being withdrawn, the bone chips being directed by the flutes into the threaded portion 22. It will be appreciated that the healing process forms bone about the shank portion 24 of the screw which is of lesser diameter than the screw-threaded portion 22. It therefore is necessary to cut through the bone grown into the annular space about the shank portion 24 provided when the screws were initially installed.

In a preferred embodiment of the present invention, the end surfaces 36 at the tip 20 of the screw form an angle, preferably about 17°, with a plane passing perpendicular through the axis of the screw. As previously indicated, the outer surfaces 38 of the tip portion form an angle preferably about 6° but within a range of 5°-7°. The screw may be provided in various lengths, for example, the screw may have a length 3 to 4 inches and a diameter at the shank of 0.198 inch. The threaded portion may have a diameter of 0.265 inches. The threads may have a pitch of 0.0713 inch, with a land of 0.040 inch therebetween. The flank of the threads may be 60°. The cannula may have a diameter of 0.130 inches. The underside of the head has a 0.187 radius and the length of the hex nut may be 0.135. The exterior surface 38 from point 32 to the bottom of end surface 36 is 0.060 inches.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A cannulated self-tapping, self-drilling screw for orthopedic bone surgery comprising:
    an elongated shaft having an elongated axis and tip, head, self-tapping screw-threaded, and shank portions, said screw-threaded portion being disposed adjacent said tip portion and said shank portion being disposed between said head and said screw-threaded portions, said shaft defining a cannula extending coaxially through said shaft an opening through said tip and said head portions;
    a plurality of flutes formed in said screw-threaded portion at circumferentially spaced positions thereabout and interrupting the threads thereof to define self-tapping cutting edges along the interrupted threads for threading the screw into the bone;
    said tip portion including a pair of circumferentially spaced cutting points at the distal end of said tip potion;
    the distal end of said tip portion having end surfaces facing generally axially of said screw with each end surface extending from a cutting point at a predetermined angle circumferentially about said screw to terminate at a circumferentially adjacent cutting edge at a location axially inwardly of the point of said adjacent cutting edge and in alignment therewith in an axial direction;
    the outer surface of said screw between each said point and the first of said self-tapping screw threads of said tip portion extending circumferentially about said screw, terminating at a circumferentially adjacent flute and being tapered in an axial direction to form an angle of between about 5-7 degrees with the axis of said screw.

2. A screw according to claim 1 wherein said outer surfaces form angles of about 6 degrees with the axis of said screw.

3. A screw according to claim 1 wherein said head portion has a larger diameter than said shank portion and has external flats thereabout for receiving a tool whereby the screw may be rotated.

4. A screw according to claim 1 wherein said threaded portion has a larger diameter than said shank portion whereby debris from the cutting action of said cutting edges passes along said threaded portion and said shank portion upon threading the screw into the bone.

5. A screw according to claim 1 including at least a pair of reverse cutting flutes disposed in said threaded portion of a said screw, said reverse cutting flutes being circumferentially spaced one from the other, spaced axially from said plurality of flutes and interrupting said threaded portion to define reverse cutting edges for cutting bone upon unthreading said screw from said bone.

6. A screw according to claim 5 wherein the cutting edges of said reverse cutting flutes lie at positions spaced circumferentially from the cutting edges of said plurality flutes.

7. A screw according to claim 5 wherein said end surfaces form an angle of about 17 degrees with a perpendicular to the axis of the screw.

8. A screw according to claim 7 wherein said reverse cutting flutes extend through the last thread of said threaded portion toward said shank portion and provide direct communication with said shank portion whereby debris from the cutting action of said reverse cutting edges, upon unthreading the screw from the bone, passes along said threaded portion and said shank portion for egress.

9. A screw according to claim 1 wherein said self-tapping cutting edges terminate at the distal end of said screw in said cutting points, respectively.

10. A cannulated self-tapping, self-drilling screw for orthopedic bone surgery comprising:
    an elongated shaft having an elongated axis and tip, head, self-tapping screw-threaded, and shank portions, said screw-threaded portion being disposed adjacent said tip portion and said shank portion disposed between said head and said screw-threaded portions, said shaft defining a cannula extending coaxially through said shaft and opening through said tip and said head portions;

a plurality of flutes formed in said screw-threaded portion at circumferentially spaced positions thereabout and interrupting the threads thereof to define self-tapping cutting edges along the interrupted threads for threading the screw into the bone, a portion of said flutes defining said cutting edges being curved in a circumferential direction about the axis of said screw to direct bone chips cut by said cutting edges, upon threading the screw into the bone, into said screw-threaded portion and facilitate removal of the bone chips;

said tip portion including a pair of circumferentially spaced cutting points at the distal end thereof;

the outer surface of said screw between each said point and the first of said self-tapping screw threads of said tip portion extending circumferentially about said screw and forming an angle of between about 5-7 degrees with the axis of said screw;

at least a pair of reverse cutting flutes disposed in said threaded portion of a said screw, said reverse cutting flutes being circumferentially spaced one from the other, spaced axially from said plurality of flutes and interrupting said threaded portion to define reverse cutting edges for cutting bone upon unthreading said screw from said bone.

11. A screw according to claim 10 wherein said outer surfaces form angles of about 6 degrees with the axis of said screw.

12. A screw according to claim 11 wherein said head portion has a larger diameter than said shank portion and has external flats thereabout for receiving a tool whereby the screw may be rotated.

13. A screw according to claim 11 wherein said threaded portion has a larger diameter than said shank portion whereby debris from the cutting action of said cutting edges passes along said threaded portion and said shank portion upon threading the screw into the bone.

14. A screw according to claim 11 wherein the cutting edges of said reverse cutting flutes lie at positions spaced circumferentially from the cutting edges of said plurality flutes.

15. A screw according to claim 11 including end surfaces at said tip portion of said screw and facing axially of said screw forming an angle of about 17 degrees with a perpendicular to the axis of the screw.

16. A screw according to claim 15 wherein said reverse cutting flutes extend through the last thread of said threaded portion toward said shank portion and provide direct communication with said shank portion whereby debris from the cutting action of said reverse cutting edges, upon unthreading the screw from the bone, passes along said threaded portion and said shank portion for egress.

17. A screw according to claim 1 wherein a surface portion of the flutes defining the cutting edges thereof are curved in a circumferential direction about the axis of said screw to direct bone chips cut by said cutting edges, upon threading the screw into the bone, into said screw-threaded portion and facilitate removal of the bone chips, the surface portions being curved circumferentially in the direction of threading the screw into the bone.

18. A screw according to claim 17 including at least a pair of reverse cutting flutes disposed in said threaded portion of said screw, said reverse cutting flutes being circumferentially spaced one from the other, spaced axially from said plurality of flutes and interrupting said threaded portion to define reverse cutting edges for cutting bone upon unthreading said screw from said bone, said reverse cutting flutes having surface portions thereof defining said reverse cutting edges curved in a circumferential direction about the axis of said screw to direct bone chips cut by said reverse cutting edges, upon unthreading said screw, into said screw-threaded portion, the curved surface portions of said reverse cutting flutes being curved circumferentially in the direction of unthreading the screw from the bone.

* * * * *